US008633156B2

(12) United States Patent
Habermann et al.

(10) Patent No.: US 8,633,156 B2
(45) Date of Patent: Jan. 21, 2014

(54) INSULIN DERIVATIVES HAVING AN EXTREMELY DELAYED TIME-ACTION PROFILE

(75) Inventors: Paul Habermann, Frankfurt am Main (DE); Gerhard Seipke, Frankfurt am Main (DE); Roland Kurrle, Frankfurt am Main (DE); Gunter Muller, Frankfurt am Main (DE); Mark Sommerfeld, Frankfurt am Main (DE); Norbert Tennagels, Frankfurt am Main (DE); Georg Tschank, Frankfurt am Main (DE); Ulrich Werner, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/820,727

(22) Filed: Jun. 22, 2010

(65) Prior Publication Data
US 2011/0173722 A1 Jul. 14, 2011

Related U.S. Application Data

(63) Continuation of application No. PCT/EP2009/000018, filed on Jan. 6, 2009.

(60) Provisional application No. 61/044,662, filed on Apr. 14, 2008.

(30) Foreign Application Priority Data

Jan. 9, 2008 (DE) .......................... 10 2008 003 566
May 24, 2008 (DE) .......................... 10 2008 025 007

(51) Int. Cl.
*A61K 38/28* (2006.01)
*A61K 38/26* (2006.01)
(52) U.S. Cl.
USPC ................ 514/5.9; 514/6.2; 514/6.3; 514/7.2
(58) Field of Classification Search
None
See application file for complete search history.

(56) References Cited

U.S. PATENT DOCUMENTS

| | | | |
|---|---|---|---|
| 5,008,241 A | 4/1991 | Markussen et al. | |
| 5,597,796 A | 1/1997 | Brange | |
| 5,656,722 A | 8/1997 | Dorschug et al. | |
| 6,100,378 A | 8/2000 | Dorschug et al. | |
| 6,444,641 B1 * | 9/2002 | Flora .............................. | 514/6.2 |
| 7,544,657 B2 * | 6/2009 | Ebbehoj et al. ................ | 514/1.1 |
| 2005/0171009 A1 | 8/2005 | Brunner-Schwarz et al. | |
| 2006/0014678 A1 * | 1/2006 | Cowley et al. .................. | 514/12 |
| 2006/0019347 A1 * | 1/2006 | Cho et al. ...................... | 435/69.1 |
| 2006/0194719 A1 * | 8/2006 | Ebbehoj et al. ................ | 514/12 |

FOREIGN PATENT DOCUMENTS

| | | |
|---|---|---|
| CN | 1276731 A | 12/2000 |
| EP | 0 194 864 A2 | 9/1986 |
| EP | 368187 A2 | 5/1990 |
| EP | 0668282 | 8/1995 |
| EP | 1 364 029 B1 | 12/2005 |
| EP | 1 222 207 B1 | 12/2007 |
| JP | 61-212598 A | 9/1986 |
| JP | 63-99096 A | 4/1988 |
| JP | 2-218696 A | 8/1990 |
| JP | 3504240 A | 9/1991 |
| JP | 6-506444 A | 7/1994 |
| JP | 2001-521004 A | 11/2001 |
| TW | 157005 B | 5/1991 |
| TW | 562806 B | 11/2003 |
| WO | WO 88/06599 A1 | 9/1988 |
| WO | WO 89/10937 | 11/1989 |
| WO | WO 90/11299 | 10/1990 |
| WO | WO 91/03550 | 3/1991 |
| WO | WO92/12999 A1 | 8/1992 |
| WO | 96/34882 A1 | 11/1996 |
| WO | WO 98/08871 | 3/1998 |
| WO | 99/21573 | 5/1999 |
| WO | WO 01/04156 | 1/2001 |
| WO | WO 01/25278 | 4/2001 |
| WO | WO 02/065985 | 8/2002 |
| WO | WO 02/068660 | 9/2002 |
| WO | WO 02/070722 | 9/2002 |
| WO | WO 02/079250 | 10/2002 |
| WO | WO 03/053339 | 7/2003 |
| WO | WO 2004/005342 | 1/2004 |
| WO | 2004/096854 A2 | 11/2004 |
| WO | 2006/029634 A2 | 3/2006 |
| WO | WO 2006/058620 | 6/2006 |
| WO | WO 2007/031187 | 3/2007 |

(Continued)

OTHER PUBLICATIONS

Markussen, J., et. al., Soluble, Prolonged-Acting Insulin Derivatives. III. Degree of Protraction, Crystallizability and Chemical Stability of Insulins Substituted in Positions A21, B13, B23, B27 and B30, Protein Engineering (1988) vol. 2., pp. 157-166.
Jekel, P. A., et. al., Use of Endoproteinase Lys-C From Lysobacter Enzymogenes in Protein Sequence Analysis, Analytical Biochemistry, vol. 134, pp. 347-354, (1983).
Kohn, W. D., et. al., PI-Shifted Insulin Analogs With Extended in Vivo Time Action and Favorable Receptor Selectivity, Peptides, vol. 28, (2007) pp. 935-948.
Kaarsholm N.C. et al., "Engineering Stability of the Insulin Monomer Fold with Application to Structure-Activity Relationships", *Biochemistry* 32(40):10773-10778 (Oct. 12, 1993).

(Continued)

Primary Examiner — Gyan Chandra
(74) *Attorney, Agent, or Firm* — Scully, Scott, Murphy & Presser, P.C.

(57) ABSTRACT

The invention relates to novel insulin analogs having a basal time-action profile, which are characterized by the addition and/or substitution of negatively and positively charged amino acid residues and by an amidation of the C-terminal carboxy group of the B chain and histidine in position 8 of the insulin A chain. The invention also relates to the production and use thereof.

27 Claims, 1 Drawing Sheet

(56) References Cited

FOREIGN PATENT DOCUMENTS

| WO | 2007/081821 A2 | 7/2007 |
|----|----------------|--------|
| WO | WO 2007/081824 | 7/2007 |
| WO | 2009/087081 A2 | 7/2009 |

OTHER PUBLICATIONS

Markussen, J. et al., "Soluble, prolonged-acting insulin derivatives. I. Degree of protraction and crystallizability of insulins substituted in the termini of the B-chain" Protein Engineering (Jun. 1987) pp. 205-213, vol. 1, No. 3.

Markussen, J. et al., "Soluble, prolonged-acting insulin derivatives. II. Degree of protraction and crystallizability of insulins substituted in positions A17, B8, B13, B27 and B30" Protein Engineering (Jun. 1987) pp. 215-223, vol. 1, No. 3.

English Translation of an Official Action dated Dec. 14, 2012, received from the Russian Patent Office, in Russian Patent Application No. 2010 133 233.

English Translation of an Official Action dated Apr. 29, 2013, received from the Russian Patent Office, in Russian Patent Application No. 2010 133 233.

English translation of Taiwanese Search Report corresponding to ROC Patent Appln. No. 0981000283; dated Oct. 7, 2013.

Japanese Notification of Reasons for Refusal corresponding to Japanese Patent Appln. No. 2010-541744, dated Sep. 10, 2013 together with English language translation.

* cited by examiner

INSULIN DERIVATIVES HAVING AN EXTREMELY DELAYED TIME-ACTION PROFILE

CROSS REFERENCE TO RELATED APPLICATIONS

This application is a continuation of International application No. PCT/EP2009/000,018, filed Jan. 6, 2009, which is incorporated herein by reference in its entirety; which claims the benefit of U.S. Provisional Application No. 61/044,662, filed Apr. 14, 2008 and the benefit of priority of German Patent Application No. 10 2008 003 566.1, filed Jan. 9, 2008 and the benefit of priority of German Patent Application No. 10 2008 025 007.4, filed May 24, 2008.

BACKGROUND OF THE INVENTION

1. Field of the Invention

The invention relates to novel insulin analogues with basal time/action profile, their preparation and use.

2. Description of the Art

The incidence of diabetes has increased in recent years to an almost epidemic extent. The disorder may result in a serious shortening of life expectancy. People with diabetes must frequently supply their body with insulin from outside. It is sensible to optimize the treatment with insulin. Different insulins with specific pharmacological properties are now available. In practice, the different insulins are differentiated according to their duration of action into short-acting insulins, fast-acting insulins, long-acting insulins and mixed insulins. Designations used synonymously for long-acting insulins are slow insulins, depot insulin or else basal insulin. The active ingredients in many of these insulin products are so-called insulin analogues which have been derived from human insulin by substitution, deletion and/or addition of one or more amino acids. The terms "insulin analogues" and "insulins" are used synonymously herein.

The policy of intensified insulin therapy attempts to diminish the health risk by aiming at a stable control of the blood glucose level by early administration of basal insulins. One example of a current basal insulin is the medicament Lantus® (active ingredient: insulin glargine=Gly (A21), Arg (B31), Arg (B32) human insulin). The general aim of developing novel, improved basal insulins is to minimize the number of hypoglycemic events. An ideal basal insulin in this connection is one acting reliably for at least 24 hours in each patient. The insulin effect ideally has a delayed onset and a time/action profile which is as shallow as possible, so that the risk of brief hypoglycemia is distinctly minimized and administration is even possible without previous intake of foodstuffs. There is a good supply of basal insulin when the insulin effect persists at the same level for as long as possible, i.e. the body is supplied with a constant amount of insulin. The risk of hypoglycemic events is thus low and a patient- and a day-specific variability is minimized. The pharmacokinetic profile of an ideal basal insulin should thus be characterized by a delayed onset of action and by a delayed, i.e. long-lasting and uniform, action.

However—despite the therapeutic advantages already achieved—none of the slow insulins described to date shows the pharmacokinetic properties of an ideal basal insulin. Desirable insulins have such a shallow and long-lasting time/action profile that the risk of hypoglycemic events and of the day-dependent variations in the patient is further minimized and the duration of action is further delayed, so that it is no longer necessary in some circumstances to administer insulin daily. This would make simplified treatment of diabetics possible, especially of elderly diabetics and those in need of care, who are no longer able to inject insulin themselves, and would thus also be of great economic benefit. Such basal insulins would additionally be beneficial in the early phase of type 2 diabetes. Clinicians report that the injection phobia present in many people deters them from starting insulin therapy in good time. As a consequence, the control of blood glucose is poor, leading to the late sequelae of diabetes. A basal insulin which reduces the number of insulin doses given by injection might have the effect of making insulin therapy more acceptable to patients.

Kohn et al. (Peptides 28 (2007) 935-948) describe how it is possible to optimize the pharmacodynamics of insulin by preparing insulin analogues whose isoelectric point (pI) is shifted, by addition of lysine or arginine at the B chain end or at the N terminus of the A and B chain, in the direction of the alkaline range compared with the isoelectric point of human insulin (pI=5.6), so that the solubility under physiological conditions is reduced and a prolonged time/action profile results. Compound 18 from Kohn et al. (Arg (A0), Gly (A21), Arg (B31), Arg (B32) human insulin (experimentally determined pI=7.3; calculated pI=7.58) is described in this connection as the best compound in the context of the idea. Kohn et al. therefore regard the main aim in designing novel insulin analogues as being the addition of positively charged amino acids to the amino acid sequence of human insulin for the purpose of increasing the isoelectric point from pI=5.6 into the neutral range.

However, it has now surprisingly been found that the described desirable basal time/action profile is obtained with insulin analogues which are characterized by the features that
- the B chain end consists of an amidated basic amino acid residue such as lysine or argininamide, i.e. in the amidated basic amino acid residue at the B chain end the carboxyl group of the terminal amino acid is present in its amidated form, and
- the A8 amino acid position is occupied by a histidine residue, and
- the A21 amino acid position is occupied by a glycine residue, alanine residue, serine residue or threonine residue, and
- no more than one amino acid residue of the group comprising A5, A15, A18, B-1, B0, B1, B2, B3 and B4 corresponds to Asp or Glu.

Surprisingly, precisely the insulin analogues described have the desired advantageous time/action profiles approaching the ideal, i.e. a delayed shallow onset of action and a longer duration of action. The risk of hypoglycemic events is thus distinctly minimized. The delay is so marked that it is surprisingly possible to detect the effect even in model experiments on rats. The delayed action of insulin glargine cannot by contrast be unambiguously observed in rats, as shown in FIG. 2. FIG. 1 shows the hypoglycemic effect of the compound YKL202 and YKL203 of the invention. The results obtained in the experiment on rats are confirmed in an experiment on dogs. Once again, the duration of action is observed to be distinctly longer than that of insulin glargine. Thus, novel basal insulins which need to be administered distinctly less frequently have been provided. Besides these pharmacokinetic advantages described, the analogues of the invention show better properties compared with insulin glargine in pharmacological respects. Moreover, the claimed insulins also show advantages in physicochemical respects.

SUMMARY OF THE INVENTION

It has now surprisingly been found that insulin analogues of the formula I

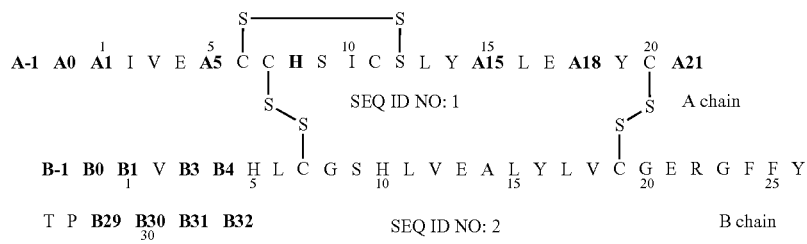

where
A-1 corresponds to Lys, Arg or an amino group;
A0 corresponds to Lys, Arg or a chemical bond;
A1 corresponds to Arg or Gly;
A5 corresponds to Asp, Glu or Gln;
A15 corresponds to Asp, Glu or Gln;
A18 corresponds to Asp, Glu or Asn;
A21 corresponds to Ala, Ser, Thr or Gly;
B-1 corresponds to Asp, Glu or an amino group;
B0 corresponds to Asp, Glu or a chemical bond;
B1 corresponds to Asp, Glu, Phe or a chemical bond;
B3 corresponds to Asp, Glu or Asn;
B4 corresponds to Asp, Glu or Gln;
B29 corresponds to Arg, Lys or an amino acid selected from the group comprising the amino acids Phe, Ala, Thr, Ser, Val, Leu, Glu or Asp, or a chemical bond;
B30 corresponds to Thr or a chemical bond;
B31 corresponds to Arg, Lys or a chemical bond;
B32 corresponds to Arg-amide or Lys-amide.
where no more than one amino acid residue of the group comprising A5, A15, A18, B-1, B0, B1, B2, B3 and B4 corresponds to Asp or Glu, have the desired pharmacological profile, i.e. a delayed onset of action and by a longer-lasting and uniform effect. The invention therefore relates to these insulin analogues.

DETAILED DESCRIPTION OF THE INVENTION

Figure 1:
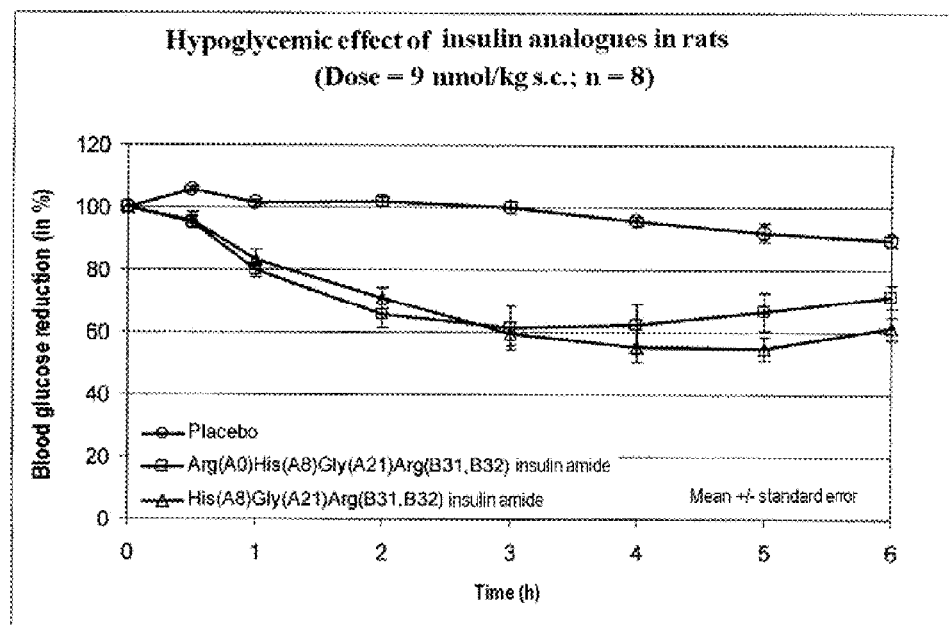
FIG. 1 shows hypoglycemic effect of insulin analogues in rats (Dose=9 nmol/kg s.c.; n=8).

The invention further relates to an insulin analogue as described above, where one amino acid residue of the group comprising A5, A15, A18, B-1, B0, B1, B2, B3 and B4 corresponds to Asp or Glu.
The invention further relates to an insulin analogue as described above, where, preferably, A-1 corresponds to Arg, A0 corresponds to Arg, A5 corresponds to Glu, A15 corresponds to Glu, A18 corresponds to Asp, A8 corresponds to His, A21 corresponds to Gly, B0 corresponds to Glu, B3 corresponds to Asp, B4 corresponds to Glu, B30 corresponds to Arg or B30 corresponds to Lys.
The invention further relates to an insulin analogue as described above, where this is selected from a group comprising
Arg (A-1), Arg (A0), Glu (A5), His (A8), Gly (A21), Arg (B30)-NH$_2$ human insulin,
Arg (A-1), Arg (A0), Glu (A5), His (A8), Gly (A21), Lys (B30)-NH$_2$ human insulin,
Arg (A-1), Arg (A0), Glu (A15), His (A8), Gly (A21), Arg (B30)-NH$_2$ human insulin,
Arg (A-1), Arg (A0), Glu (A15), His (A8), Gly (A21), Lys (B30)-NH$_2$ human insulin,
Arg (A-1), Arg (A0), Asp (A18), His (A8), Gly (A21), Arg (B30)-NH$_2$ human insulin,
Arg (A-1), Arg (A0), Asp (A18), His (A8), Gly (A21), Arg (B30)-NH$_2$ human insulin,
Arg (A-1), Arg (A0), His (A8), Gly (A21), Glu (B0), Arg (B30)-NH$_2$ human insulin,
Arg (A-1), Arg (A0), His (A8), Gly (A21), Glu (B0), Lys (B30)-NH$_2$ human insulin,
Arg (A-1), Arg (A0), His (A8), Gly (A21), Asp (B3), Arg (B30)-NH$_2$ human insulin,
Arg (A-1), Arg (A0), His (A8), Gly (A21), Asp (B3), Lys (B30)-NH$_2$ human insulin,
Arg (A-1), Arg (A0), His (A8), Gly (A21), Glu (B4), Arg (B30)-NH$_2$ human insulin,
Arg (A-1), Arg (A0), His (A8), Gly (A21), Glu (B4), Lys (B30)-NH$_2$ human insulin,
Arg (A0), His (A8), Gly (A21), Arg (B31), Arg (B32)-NH$_2$-human insulin,
Arg (A0), His (A8), Gly (A21), Arg (B31), Lys (B32)-NH$_2$-human insulin,
Arg (A0), Glu (A5), His (A8), Gly (A21), Arg (B31), Arg (B32)-NH$_2$-human insulin,
Arg (A0), Glu (A5), His (A8), Gly (A21), Arg (B31), Lys (B32)-NH$_2$-human insulin,
Arg (A0), Asp (A18), His (A8), Gly (A21), Arg (B31), Arg (B32)-NH$_2$-human insulin,
Arg (A0), Asp (A18), His (A8), Gly (A21), Arg (B31), Lys (B32)-NH$_2$-human insulin,
Arg (A0), Glu (A15), His (A8), Gly (A21), Arg (B31), Arg (B32)-NH$_2$-human insulin,
Arg (A0), Glu (A15), His (A8), Gly (A21), Arg (B31), Lys (B32)-NH$_2$-human insulin,
Arg (A0), His (A8), Gly (A21), Asp (B3), Arg (B31), Arg (B32)-NH$_2$-human insulin,
Arg (A0), His (A8), Gly (A21), Asp (B3), Arg (B31), Lys (B32)-NH$_2$-human insulin,
Arg (A0), His (A8), Gly (A21), Glu (B4), Arg (B31), Arg (B32)-NH$_2$-human insulin,
Arg (A0), His (A8), Gly (A21), Glu (B4), Arg (B31), Lys (B32)-NH$_2$-human insulin,
Arg (A0), His (A8), Gly (A21), Glu (B0), Arg (B31), Arg (B32)-NH$_2$-human insulin,
Arg (A0), His (A8), Gly (A21), Glu (B0), Arg (B31), Lys (B32)-NH$_2$-human insulin,
Arg (A0), His (A8), Gly (A21), Arg (B30)-NH$_2$-human insulin,
Arg (A0), His (A8), Gly (A21), Lys (B30)-NH$_2$-human insulin,
Arg (A-1), Arg (A0), His (A8), Gly (A21), Arg (B30)-NH$_2$-human insulin, Arg (A-1), Arg (A0), His (A8), Gly (A21), Lys (B30)-NH$_2$-human insulin,
Arg (A0), Arg (A1), His (A8), Gly (A21), Arg (B30)-NH$_2$-human insulin,
Arg (A0), Arg (A1), His (A8), Gly (A21), Lys (B30)-NH$_2$-human insulin,
His (A8), Gly (A21), Arg (B31), Arg (B32)-NH$_2$-human insulin.

Specification of the term "human insulin" in the designations of the insulin analogues mentioned makes reference to the amino acid sequences of the A chain and B chain of human insulin, and all deviations (additions, substitutions, deletions) therefrom are indicated in a given designation of an insulin analogue.

The invention further relates to a process for preparing an insulin analogue as described above, where a precursor of the insulin analogue is prepared recombinantly, the precursor is processed enzymatically to two-chain insulin, and a coupling with argininamide is carried out in the presence of an enzyme having trypsin activity, and the insulin analogue is isolated.

The invention further relates to the use of an insulin analogue as described above for the manufacture of a medicament for the treatment of diabetes mellitus, in particular of diabetes mellitus of type I or type II.

The invention further relates to a pharmaceutical comprising an insulin analogue as described above and/or physiologically acceptable salts thereof.

The invention further relates to a pharmaceutical comprising an insulin analogue as described above which is employed therapeutically for cartilage regeneration.

The invention further relates to a pharmaceutical comprising an insulin analogue as described above which is employed therapeutically for assisting beta cell regeneration.

The invention further relates to a formulation of the insulin analogue as described above, where the formulation is in aqueous form comprising the dissolved insulin analogue.

The invention further relates to a formulation of the insulin analogue as described above, where the formulation is in the form of powder, in particular in crystalline and/or amorphous form.

The invention further relates to a formulation of the insulin analogue as described above, where the formulation is in the form of a suspension.

The invention further relates to a formulation of the insulin analogue as described above, where the formulation additionally comprises a chemical chaperone.

The invention further relates to a DNA coding for a precursor of an insulin analogue as described above.

The invention further relates to a DNA coding for the A chain of an insulin analogue as described above.

The invention further relates to a DNA coding for the B chain of an insulin analogue as described above.

The invention further relates to a vector comprising a DNA as described above.

The invention further relates to a host organism comprising a DNA as described above or a vector as described above.

The invention further relates to a preproinsulin analogue, wherein the C peptide carries the amino acid residue arginine at its N terminus and its C terminus is characterized by the form Arg Arg, Arg Lys or Lys Arg Arg.

The invention further relates to a formulation as described above which additionally comprises also a glucagon-like peptide-1 (GLP1) or an analogue or derivative thereof, or exendin-3 or -4 or an analogue or derivative thereof, preferably exendin-4.

The invention further relates to a formulation as described above in which an analogue of exendin-4 is selected from a group comprising
H-desPro$^{36}$-exendin-4-Lys$_6$-NH$_2$,
H-des(Pro$^{36,37}$)-exendin-4-Lys$_4$-NH$_2$ and
H-des(Pro$^{36,37}$)-exendin-4-Lys$_5$-NH$_2$,
or a pharmacologically tolerable salt thereof.

The invention further relates to a formulation as described above in which an analogue of exendin-4 is selected from a group comprising
desPro$^{36}$ [Asp$^{28}$]exendin-4 (1-39),
desPro$^{36}$ [IsoAsp$^{28}$]exendin-4 (1-39),
desPro$^{36}$ [Met(O)$^{14}$, Asp$^{28}$]exendin-4 (1-39),
desPro$^{36}$ [Met(O)$^{14}$, IsoAsp$^{28}$]exendin-4 (1-39),
desPro$^{36}$ [Trp(O$_2$)$^{25}$, Asp$^{28}$]exendin-2 (1-39),
desPro$^{36}$ [Trp(O$_2$)$^{25}$, IsoAsp$^{28}$]exendin-2 (1-39),
desPro$^{36}$ [Met(O)$^{14}$Trp(O$_2$)$^{25}$, Asp$^{28}$]exendin-4 (1-39) and
desPro$^{36}$ [Met(O)$^{14}$Trp(O$_2$)$^{25}$, IsoAsp$^{28}$]exendin-4 (1-39),
or a pharmacologically tolerable salt thereof.

The invention further relates to a formulation as described in the preceding paragraph, in which the peptide -Lys$_6$-NH$_2$ is attached to the C termini of the analogues of exendin-4.

The invention further relates to a formulation as described above in which an analogue of exendin-4 is selected from a group comprising
H-(Lys)$_6$-des Pro$^{36}$ [Asp$^{28}$]exendin-4(1-39)-Lys$_6$-NH$_2$
des Asp$^{28}$Pro$^{36}$, Pro$^{37}$, Pro$_{38}$ exendin-4(1-39)-NH$_2$,
H-(Lys)$_6$-des Pro$^{36}$, Pro$^{37}$, Pro$^{38}$ [Asp$^{28}$]exendin-4(1-39)-NH$_2$,
H-Asn-(Glu)$_5$ des Pro$^{36}$, Pro$^{37}$, Pro$^{38}$ [Asp$^{28}$]exendin-4(1-39)-NH$_2$,
des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$, Pro$^{37}$, Pro$^{38}$ [Asp$^{28}$]exendin-4(1-39)-(Lys)$_6$-NH$_2$,
H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$ [Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Trp(O$_2$)$^{25}$]exendin-4(1-39)-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-NH$_2$,
des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$]exendin-4(1-39)-NH$_2$,
des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$]exendin-4(1-39)-Lys$_6$-NH$_2$,
H-Asn-(Glu)$_5$ des Pro$^{36}$, Pro$^{37}$, Pro$^{38}$ [Met(O)$^{14}$, Asp$^{28}$] exendin-4(1-39)-(Lys)$_6$-NH$_2$,
H-(Lys)$_6$-des Pro$^{36}$ [Met(O)$^{14}$, Trp(O$_2$)$^{25}$, Asp$^{28}$]exendin-4 (1-39)-Lys$_6$-NH$_2$, des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36'}$ Pro$^{37}$, Pro$^{38}$ [Met(O)$^{14}$, Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$,
des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-(Lys)$_6$-des Pro$^{36'}$ Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$,
or a pharmacologically tolerable salt thereof.

The invention further relates to a formulation as described above which additionally comprises Arg$^{34}$, Lys$^{26}$ (N$^\epsilon$($\gamma$-glutamyl(N$^\alpha$-hexadecanoyl))) GLP-1 (7-37) [liraglutide] or a pharmacologically tolerable salt thereof.

It is clear to a skilled worker in this connection that the insulins of the invention may be item of a pharmaceutical formulation which has an advantageous effect after administration. Aqueous solutions are the starting point in this connection. Further components must accordingly be miscible. The risk of viral animal contamination is minimized in that the preparation ought not to comprise any components derived from animal sources. It is further advantageous to prevent microbial contamination by adding preservatives. It is possible by adding isotonic agents to compensate for a possible negative effect of the formulation on the physiology of the tissue cells at the administration site. The addition of protamine may have a stabilizing effect, so that substantially salt-free insulin preparation can be obtained by adding protamine to the formulation. Addition of a phenolic component may lead to stabilization of the structure of the insulin analogue used and thus additionally bring about inter alia the delaying effect on the onset of action. It is also possible to add to the formulation substances which stabilize the spatial structure of the slow insulins of the invention and lead to better thermal stability. Such chemical chaperones may be for example short synthetic peptides, which may also comprise amino acid analogues or include for example peptide sequences derived from the C peptide of insulin.

The insulins of the invention can be incorporated into nanoparticles for developing depot forms. Also conceivable are so-called slow release formulations in which the slow insulin of the invention is present reversibly bound to a polymer carrier.

The insulins of the invention can be administered in parallel with fast-acting insulin such as insulin glulisine (APIDRA®), NovoRapid®, insulin lispro (HUMALOG®) or insulin derivatives undergoing development or formulations with an appropriate time/action profile or inhalable insulin or nasally or orally administered insulins which are undergoing development. It will be clear to a skilled worker in this connection that appropriately formulated mixtures of fast-acting and slow insulin of the invention can also be used for this purpose. The insulin analogues of the invention can further be used in pharmaceutical preparations which comprise peptides which are described by an activity comparable to GLP-1 (glucagon like Peptide-1) or exendin-4 or exendin-3. GLP-1 (7-37), exenatide (BYETTA®) or peptides whose preparation is described in the patent applications WO 2006/058620, WO 2001/04156, WO 2004/005342 and WO 98/08871 represent examples of such peptides. Formulations particularly advantageous in this connection are those comprising a depot formulation of these peptides. Types of therapy advantageous especially in the initial phase of type II diabetes are those which provide in parallel with the administration of the pharmaceuticals of the invention, which increase the effect of insulin, such as, for example, metformin. Combination therapies with dipeptidyl peptidase-4 inhibitors which increase the level of incretins are, like combinations with sulfonylureas which increase insulin secretion in the pancreas, likewise possible. The slow insulins of the invention can be employed particularly advantageously when regeneration of beta cells from appropriate stem cells is initiated by administration of differentiation factors. All these applications are mentioned by way of example for the therapy of diabetes, and the invention likewise relates thereto. The invention thus further relates to the use of the insulins of the invention in combination with other active ingredients for the treatment of diabetes, especially diabetes of type I or type II diabetes.

The invention also relates further to the use of the insulins of the invention in regeneration processes which relate to the skeleton, such as, for example, cartilage regeneration. It is important in this use to make controlled use of the mitogenic potential of insulins without at the same time eliciting a strong metabolic reaction.

The invention further relates to a pharmaceutical which comprises an analogue of the invention which represents in particular an aqueous formulation or a powder.

The pharmaceutical is a pharmaceutical preparation which is preferably a solution or suspension for injection purposes; it is characterized by a content of at least one insulin analogue of the invention, and/or at least one of the physiologically tolerated salts thereof in dissolved, amorphous and/or crystalline—preferably in dissolved—form.

The preparation preferably has a pH of between about 2.5 and 8.5, in particular between 4.0 and 8.5, comprises a suitable tonicity agent, a suitable preservative and, where appropriate, a suitable buffer, and preferably also a particular zinc ion concentration, in sterile aqueous solution. The totality of the preparation ingredients apart from the active ingredient forms the preparation carrier. Suitable tonicity agents are for example glycerol, glucose, mannitol, NaCl, calcium or magnesium compounds such as CaCl$_2$ etc. The solubility of the insulins of the invention or the physiologically tolerated salts thereof at weakly acidic pH values is influenced by the choice of the tonicity agent and/or preservative.

Examples of suitable preservatives are phenol, m-cresol, benzyl alcohol and/or p-hydroxybenzoic esters.

Buffer substances which can be used in particular for adjusting a pH between about 4.0 and 8.5 are for example sodium acetate, sodium citrate, sodium phosphate etc. Otherwise, physiologically acceptable dilute acids (typically HCl) or alkalis (typically NaOH) are also suitable for adjusting the pH.

If the preparation has a zinc content, preference is given to one of from 1 µg/ml to 2 mg/ml, in particular from 1 µg/ml to 200 µg zinc/ml. The action profile of the insulin analogues of the invention can surprisingly be influenced satisfactorily by addition of zinc. This allows the production of preparations which differ in relation to the total duration of action, the speed of onset of action and the profile of the effect curve, thus allowing an individual stabilization of the patient.

For the purpose of varying the active ingredient profile of the preparation of the invention it is also possible to admix unmodified insulin, preferably bovine, porcine or human insulin, especially human insulin, or insulin analogues and derivatives thereof. It is likewise possible to admix one or more exendin-4 derivatives or peptides which are characterized by an activity comparable to GLP-1 (glucagon like peptide-1). The invention likewise relates to such pharmaceuticals (preparations).

Preferred active ingredient concentrations are those corresponding to about 1-1500, more preferably about 5-1000 and in particular about 40-400 international units/ml.

The insulin analogues of the invention are initially prepared biotechnologically as precursor which does not yet include the amide. The skilled worker is familiar with a large number of possibilities for preparing insulins. Host cell systems used in this connection are bacteria, yeasts and higher plants or plant cells for cultivation by fermentation. If cost considerations permit, expression systems which use animal cells as host system are also conceivable. However, the precondition therefor is reliable freedom from animal viruses. It is thus clear that the expression systems described by way of example represent only a small segment of the host/vector systems developed for the recombinant preparation of proteins. For example, biotechnological processes based on yeast or plant systems such as mosses, algae or higher plants such as tobacco, pea, safflower, barley, corn or oilseed rape are not described in the application. Nevertheless, the invention likewise includes host/vector systems and coding DNA sequences which allow the target peptides to be prepared in appropriate biotechnological expression systems. Host organisms can thus be selected in particular from the plant kingdom from organisms of the first division Schizophyta comprising Schizomycetes, bacteria or blue algae, organisms of the $2^{nd}$ division Phycophyta class V Chlorophyceae, organisms of the $2^{nd}$ division Phycophyta class VII Rhodophyceae, organisms of the $3^{rd}$ division Mycophyta, organisms of the $5^{th}$ division Bryophyta and organisms of the $7^{th}$ division Spermatophyta.

European patent application EP-A 1 222 207 describes a plasmid pINT358d which codes for a preproinsulin which includes a modified C peptide. It is now possible with the aid of the polymerase chain reaction (PCR) to modify the proinsulin-encoding sequence specifically so that it is possible to express preproinsulins which can serve as precursors of the insulins of the invention. Corresponding fusion proteins need not necessarily be prepared intracellularly. It is clear to the skilled worker that such proteins can also be prepared by bacterial expression with subsequent secretion into the periplasm and/or into the culture supernatant. European patent application EP-A 1 364 029 describes this by way of example. The invention likewise relates to the proinsulin precursors which lead to the analogues of the invention.

The proinsulins prepared in this way can in principle be converted into an insulin analogue precursor which includes lysine or arginine in position A0 and carries lysine or arginine at the C-terminal end of the B chain. It is alternatively possible to add a positively charged amino acid semisynthetically to the N terminus of the A chain if lysine or arginine are not already present.

If the proinsulins of the invention are in the form of inclusion bodies or soluble form after intracellular expression in bacteria, these precursors must be folded by in vitro folding into the correct conformation before the processing and biochemical modification can be undertaken. In this connection, the described fusion protein allows direct folding after denaturation by means of urea or guanidinium hydrochloride, and the invention likewise relates to folding intermediates.

Biochemical methods are used to concentrate the individual intermediates, especially separation processes whose underlying principles are published and in fact the subject of textbooks. It is clear to the skilled worker that such principles can consequently be combined and thus may lead to processes which have not previously been published in their sequence. The invention thus likewise relates to processes which lead to purification of the analogues of the invention.

The invention further relates to a process for preparing the insulin analogues of the invention, where a precursor of the insulin analogue is prepared recombinantly and converted enzymatically into a two-chain insulin precursor which carries arginine or lysine N-terminally in relation to amino acid 1 of the A chain, and has at the C-terminal end of the B chain a lysine or arginine residue which is converted with argininamide or lysinamide in the presence of an enzyme having trypsin activity into the amide and thus into the slow insulin of the invention, and is prepared with high purity by a biochemical purification process.

Proteins which differ through substitution of at least one naturally occurring amino acid residue by other amino acid residues and/or addition and/or deletion of at least one amino acid residue from the corresponding, otherwise identical naturally occurring protein are referred to as "analogues" of proteins. It is also possible in this connection for the added and/or replaced amino acid residues to be ones which do not occur naturally.

Proteins which are obtained by chemical modification of certain amino acid residues of initial proteins are referred to as "derivatives" of proteins. The chemical modification may consist for example of addition of one or more particular chemical groups to one or more amino acids.

Figure 2:
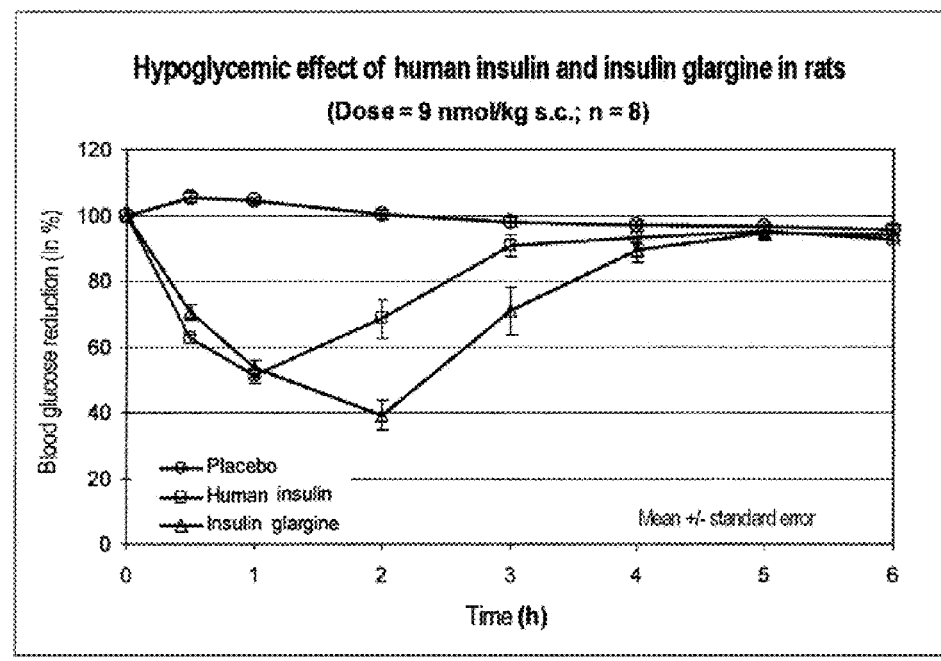
FIG. 2 shows hypoglycemic effect of human insulin and insulin glargine in rats (Dose=9 nmol/kg s.c.; n=8).

Key to Figures:
FIG. 1: Blood glucose-lowering effect of insulin analogues of the invention in rats
FIG. 2 Blood glucose-lowering effect of insulin glargine in rats The following examples are intended to illustrate the concept of the invention without having a restrictive effect in this connection.

Example 1

Preparation of the Vector Derivative pINT3580 which Codes for Gly (A21)-Insulin and a Modified C Peptide which Carries Arg Arg at the C/A Chain Boundary European patent application EP-A 1 222 207 describes the plasmids pINT358d, pINT91d and the primer sequence Tir. DNA of these products is used to construct the plasmid pINT3580. The plasmid pINT358d is moreover characterized by a gene sequence which codes for a modified C peptide having particular properties. Three primer sequences are synthesized:

```
pint3580_glya21rev
                                          (SEQ ID NO: 3)
5'-CAAAGGTCGACTATTAGCCGCAGTAGTTCTCCAGCTGG-3'
```

This primer serves after working up to introduce glycine (bold print, underlined) instead of asparagine in position 21 of the A chain of the proinsulin sequence encoded by pINT358d.

```
arg_cjuncf
                                          (SEQ ID NO: 4)
5'-GTCCCTGCAGCGTCGCGGCATCGTGGAGCAG-3'
```

This primer serves like the primer arg_cjunc_rev for introducing arginine instead of lysine at the insulin A/B chain boundary.

```
arg_cjunc_rev
                                          (SEQ ID NO: 5)
5'-CCACGATGCC GCGACGCTGC AGGGACCCCT CCAGCG-3'
```

The codon for the arginine to be introduced is in bold print in both primers.

A PCR is carried out in accordance with the European patent application EP-A 1 222 207 with each of the primer pairs Tir/arg_cjunc_rev and arg_cjuncf/pint3580_glya21rev and with DNA of the plasmid pINT358d as template. Aliquots of the products of the two reactions are combined and employed together with the primer pair Tir/pint3580_glya21rev in a third PCR. The product of this reaction is purified after fractionation of the reaction mixture by gel electrophoresis and is digested with the restriction enzymes Sal1/Nco1 in accordance with the manufacturer's instructions in one and the same reaction, the reaction mixture is fractionated by gel electrophoresis, and the DNA fragment encoding the proinsulin sequence is isolated. The fragment is then inserted by a DNA ligase reaction into the Nco1/Sal1-opened pINT91d vector DNA.

The ligation mixture is used to transform competent *E. coli* bacterial cells. The transformation mixture is taken out on selection plates which contain 25 mg/l ampicillin. Plasmid DNA is isolated from colonies and characterized by DNA sequence analysis. Correct plasmids are called pINT3580.

Example 2

Construction of the Plasmid pINT3581 Coding for His (A8), Gly (A21)-Preproinsulin The construction takes place as described in example 1 by 3 polymerase chain reactions. The product of the third reaction is inserted after Nco1/Sal1 cleavage into the Nco1/Sal1-opened pINT91d vector DNA. The primers Tir and pint3580_glya21rev are used. Two further primers are synthesized:

```
pint3580_Ha8f
                                          (SEQ ID NO: 6)
5'-AGCAGTGCTGCCACAGCATCTGCTCCCTCTAC-3' pint3580_Ha8rev
                                          (SEQ ID NO: 7)
5'-GAG CAGATGCT GTG GCAGCACTG CTCCACGATG-3'
```

The codon which codes for histidine in position 8 of the A chain is emphasized by emboldening in each case. The construction is carried out as described in example 1. Template for PCR1 and 2 is DNA of the plasmid pINT3580. PCR1 is carried out with the primer pair Tir/pint3580_Ha8rev and PCR2 is carried out with the primer pair pint3580_Ha8f/pint3580_glya21rev. With the primer pair Tir/pint3580_glya21rev is employed in PCR 3. Template in this case is a mixture of the reaction products of PCR1 and PCR2. Correct plasmids are called pINT3581.

The preproinsulin encoded by the plasmid is precursor for the compound YKL202, which is characterized as Arg (A0), His (A8), Gly (A21), Arg (B31), Arg (B32)-NH$_2$-human insulin, and which results after amidation with argininamide.

The preproinsulin encoded by the plasmid is precursor for the compound YKL202b, which is characterized as Arg (A0), His (A8), Gly (A21), Arg (B31), Lys (B32)-NH$_2$-human insulin, and which results after amidation with lysinamide.

Example 3

Construction of the Plasmid pINT3582 Coding for His (A8), Glu (A5), Gly (A21)-Preproinsulin The construction takes place as described in example 1 and 2 by 3 polymerase chain reactions. The product of the third reaction is inserted after Nco1/Sal1 cleavage into the Nco1/Sal1-opened pINT91d vector DNA. The primers Tir and pint3580_glya21rev are used. Two further primers are synthesized.

```
pint3581_Ea5f
                                          (SEQ ID NO: 8)
5'GCATCGTGGAGGAGTGCTGCCACAGCATCTG3' pint3581_Ea5rev
                                          (SEQ ID NO: 9)
5'-CTGT GGCAGCACTC CTCCACGATG CCGCGACG-3'
```

The codon which codes for glutamic acid in position 5 of the A chain is emphasized by emboldening in each case. The construction is carried out as described in example 1. Template is DNA of the plasmid pINT3581. Correct plasmids are called pINT3582.

The preproinsulin encoded by the plasmid is precursor for the compound YKL202-1, which is characterized as Arg (A0), Glu (A5), His (A8), Gly (A21), Arg (B31), Arg (B32)-NH$_2$-human insulin, and which results after amidation with argininamide.

The preproinsulin encoded by the plasmid is precursor for the compound YKL202-1b, which is characterized as Arg (A0), Glu (A5), His (A8), Gly (A21), Arg (B31), Lys (B32)-NH$_2$-human insulin, and which results after amidation with lysinamide.

Example 4

Construction of the Plasmid pINT3583 Coding for His (A8), Asp (A18), Gly(A21)-Preproinsulin The construction differs from example 1 by taking place by only one polymerase chain reaction. The product of this reaction is inserted after Nco1/Sal1 cleavage into the Nco1/Sal1-opened pINT91d vector DNA. The primer Tir is used. One further primer is synthesized:

```
pint3580_Da18rev
                                         (SEQ ID NO: 10)
5' CAAAGGTCGACTATTAGCCGCAGTAGTCCTCCAGCTGGTAGAGG
GAG 3'
```

The codon which codes for aspartic acid in position 18 of the A chain is emphasized by emboldening. Template is DNA of the plasmid pINT3581. Correct plasmids are called pINT3583.

The preproinsulin encoded by the plasmid is precursor for the compound YKL202, which is characterized as Arg (A0), Asp (A18), His (A8), Gly (A21), Arg (B31), Arg (B32)-NH$_2$-human insulin, and which results after amidation with argininamide.

The preproinsulin encoded by the plasmid is precursor for the compound YKL202-2b, which is characterized as Arg (A0), Asp (A18), His (A8), Gly (A21), Arg (B31), Lys (B32)-NH$_2$-human insulin, and which results after amidation with lysinamide.

Example 5

Construction of the Plasmid pINT3585 Coding for His (A8), Glu (A15), Gly (A21)-Preproinsulin The construction differs from example 1 by taking place by only one polymerase chain reaction. The product of this reaction is inserted after Nco1/Sal1 cleavage into the Nco1/Sal1-opened pINT91d vector DNA. The primer Tir is used. One further primer is synthesized:

```
pint3580_Ea15rev
                                       (SEQ ID NO: 11)
5'-CAAAGGTCGA CTATTAGCCG CAGTAGTTCTCCAGCTCGTA

GAGGGAGCAG ATGCTG-3'
```

The codon which codes for glutamic acid in position 15 of the A chain is emphasized by emboldening. Template is DNA of the plasmid pINT3581. Correct plasmids are called pINT3585.

The preproinsulin encoded by the plasmid is precursor for the compound YKL202-3, which is characterized as Arg (A0), Glu (A15), His (A8), Gly (A21), Arg (B31), Arg (B32)-NH$_2$-human insulin, and which results after amidation with argininamide.

The preproinsulin encoded by the plasmid is precursor for the compound YKL202-3b, which is characterized as Arg (A0), Glu (A15), His (A8), Gly (A21), Arg (B31), Lys (B32)-NH$_2$-human insulin, and which results after amidation with lysinamide.

Example 6

Construction of the Plasmid pINT3588 Coding for His (A8), Gly (A21), Asp (B3)-Preproinsulin Construction takes place as described in example 1 and 2 by 3 polymerase chain reactions. The product of the third reaction is inserted after Nco1/Sal1 cleavage into the Nco1/Sal1-opened pINT91d vector DNA. The primers Tir and pint3580_glya21rev are used. Two further primers are synthesized:

```
pint3581_Db3f
                                       (SEQ ID NO: 12)
5'-GCACGATTTGTGGACCAGCACCTGTGCGGC-3' pint3581_Db3rev
                                       (SEQ ID NO: 13)
5'-CACAGG TGCTGGTCCA CAAATCGTGC CGAATTTC-3'
```

The codon which codes for asparagine in position 3 of the insulin B chain is emphasized by emboldening in each case. Construction is carried out as described in example 1. Template is DNA of the plasmid pINT3581. Correct plasmids are called pINT3588.

The preproinsulin encoded by the plasmid is precursor for the compound YKL202-4, which is characterized as Arg (A0), His (A8), Gly (A21), Asp (B3), Arg (B31), Arg (B32)-NH$_2$-human insulin, and which results after amidation with argininamide.

The preproinsulin encoded by the plasmid is precursor for the compound YKL202-4-b, which is characterized as Arg (A0), His (A8), Gly (A21), Asp (B3), Arg (B31), Lys (B32)-NH$_2$-human insulin, and which results after amidation with lysinamide.

Example 7

Construction of the Plasmid pINT3593 Coding for His (A8), Gly (A21), Glu (B4) Preproinsulin Construction takes place as described in example 1 and 2 by 3 polymerase chain reactions. The product of the third reaction is inserted after Nco1/Sal1 cleavage into the Nco1/Sal1-opened pINT91d vector DNA. The primers Tir and pint3580_glya21rev are used. Two further primers are synthesized:

```
pint3581_Eb4f
                                       (SEQ ID NO: 14)
5'-ACGATTTGTGAACGAGCACCTGTGCGGCTC-3' pint3581_Eb4rev
                                       (SEQ ID NO: 15)
5'-CGCACAGG TGCTCGTTCA CAAATCGTGC CGAATTTC-3'
```

The codon which codes for glutamine in position 4 of the insulin B chain is emphasized by emboldening. The construction is carried out as described in example 1. Template is DNA of the plasmid pINT3581. Correct plasmids are called pINT3593.

The preproinsulin encoded by the plasmid is precursor for the compound YKL202-5, which is characterized as Arg (A0), His (A8), Gly (A21), Glu (B4), Arg (B31), Arg (B32)-NH$_2$-human insulin, and which results after amidation with argininamide.

The preproinsulin encoded by the plasmid is precursor for the compound YKL202-5b, which is characterized as Arg (A0), His (A8), Gly (A21), Glu (B4), Arg (B31), Lys (B32)-NH$_2$-human insulin, and which results after amidation with lysinamide.

Example 8

Construction of the Plasmid pINT3597 Coding for His (A8), Gly (A21), Glu (B0)-Preproinsulin Construction takes place by 2 polymerase chain reactions. The primer pint3580_glya21rev is used. Two further primers are synthesized:

```
pint3581_Eb0f1
                                       (SEQ ID NO: 16)
5'-CAACAGGAA ATTCGGCACG AGAGTTTGTG AACCAGCACC

TGTG-3' pint3581_Eb01f2
                                       (SEQ ID NO: 17)
5'-TATCGA CCAT GG CAACAACA TCAACAGGAA ATTCGGCACG

AGAG-3'
```

There is partial overlap of the two primers in this case. Pint3581_Eb0f2 contains an NcoI recognition sequence. This is depicted underlined. The codon which codes for glutamic acid in position 0 at the start of the B chain is emphasized by emboldening in each case. Template for PCR1 is DNA of the plasmid pINT3581.

PCR1 is carried out with the primer pair pint3581_Eb-1f2/pint3580_glya21rev. Template for PCR2 is the product from PCR1. PCR2 is carried out with the primer pair pint3581_Eb-1f2/pint3580_glya21rev. The product from PCR2 covers the complete preproinsulin sequence. The product of the second reaction is inserted after Nco1/Sal1 cleavage into the Nco1/Sal1-opened pINT91d vector DNA. Correct plasmids are called pINT3597.

The preproinsulin encoded by the plasmid is precursor for the compound YKL202-6, which is characterized as Arg (A0), His (A8), Gly (A21), Glu (B0), Arg (B31), Arg (B32)-NH$_2$-human insulin, and which results after amidation with argininamide.

The preproinsulin encoded by the plasmid is precursor for the compound YKL202-6b, which is characterized as Arg (A0), His (A8), Gly (A21), Glu (B0), Arg (B31), Lys (B32)-NH$_2$-human insulin, and which results after amidation with lysinamide.

Replacement of the codon for glutamic acid in position B0 by the codon of aspartic acid and following the example results in plasmids which have aspartic acid instead of glutamic acid in position B0.

Example 9

Construction of the Plasmid pINT3700 Coding for His (A8), Gly (A21), Lys (B0)-Preproinsulin The construction serves to introduce the codon for lysine instead of the codon for arginine at the boundary between presequence and start of the B chain. Construction takes place by two polymerase chain reactions. The primer pint3580_glya21rev is used. Two further primers are synthesized:

```
pint3581_Eb0f1
                                            (SEQ ID NO: 18)
5'-CAACAGGAA ATTCGGCA AAGTTTGTG AACCAGCACC

TGTG-3' pint3581_Eb01f2
                                            (SEQ ID NO: 19)
5'-TATCGA CCAT GG CAACAACA TCAACAGGAA

ATTCGGCAGAG-3'
```

There is partial overlap of the two primers in this case, and pint3581_Eb0f2 contains an NcoI recognition sequence. This is depicted underlined. The codon which codes for glutamic acid in position 0 at the start of the B chain is emphasized by emboldening in each case. Template for PCR1 is DNA of the plasmid pINT3581. PCR1 is carried out with the primer pair pint3581_Eb-1f2/pint3580_glya21rev. Template for PCR2 is the product from PCR1. PCR2 is carried out with the primer pair pint3581_Eb-1f2/pint3580_glya21rev. The product from PCR2 covers the complete preproinsulin sequence. The product of the second reaction is inserted after Nco1/Sal1 cleavage into the Nco1/Sal1-opened pINT91d vector DNA. Correct plasmids are called pINT3700.

The preproinsulin encoded by the plasmid is precursor for the compound Arg (A0), His (A8), Gly (A21), Arg (B30)-NH$_2$-human insulin. The compound is obtained by initially preparing the intermediate Arg (A0), His (A8), Gly (A21) of the Thr (B30)-human insulin by reaction with trypsin and lysyl endopeptidase C, which intermediate is subsequently converted by amidation with argininamide into the desired compound YKL202-7, which is characterized as Arg (A0), His(A8), Gly(A21), Arg (B30)-NH$_2$-human insulin.

The preproinsulin encoded by the plasmid is precursor for the compound YKL202-7b, which is characterized as Arg (A0), His (A8), Gly (A21), Lys (B30)-NH$_2$-human insulin, and which results after amidation with lysinamide.

Example 10

Construction of the Plasmid pINT3701 Coding for Gly (A21) Lys (B0)-Preproinsulin The construction serves to introduce the codon for lysine instead of the codon for arginine at the boundary between presequence and start of the B chain. Following the construction strategy from Example 9 but using DNA of the plasmid pINT358d as template for PCR1 results in the plasmid pINT3701 which, like the original plasmid pINT358d, is characterized by the boundary between C peptide and A chain being formed by the amino acid sequence Lys-Arg.

Example 11

Construction of the Plasmid pINT3702 Coding for His (A8), Gly (A21), Lys (B0)-Preproinsulin with the C Peptide According to Example 10

Following the construction plan described in Example 2 but using DNA of the plasmid pINT3701 as template results in the plasmid pINT3702.

The preproinsulin encoded by the plasmid is precursor for the compound Arg (A0), His (A8), Gly (A21), Arg (B30)-NH$_2$-human insulin. The compound is obtained by initially preparing the intermediate Arg (A0), His (A8), Gly (A21) of the Thr (B30)-human insulin by reaction only with lysyl endopeptidase C, which intermediate is subsequently converted by amidation with argininamide into the desired compound YKL202-8, which is characterized as Arg (A0), His (A8), Gly (A21), Arg (B30)-NH$_2$-human insulin.

The preproinsulin encoded by the plasmid is precursor for the compound YKL202-8b, which is characterized as Arg (A0), His (A8), Gly (A21), Lys (B30)-NH$_2$-human insulin, and which results after amidation with lysinamide.

Example 12

Preparation of the Vector Derivative pINT3703 which Codes for His (A8), Gly (A21), Lys (B0)-Preproinsulin and a Modified C Peptide which Carries the Tripeptide Lys-Arg-Arg at the C/A Chain Boundary DNA of the plasmid pINT3702 is used as template, and the primers pint3580_glya21rev and Tir are used. Two primer sequences are synthesized.

```
3702_arg_cjuncf
                                            (SEQ ID NO: 20)
5'-TGC AGAAGCGCAGAGGCATCGTG GAGCAGTGC-3'
```

This primer serves like the primer arg_cjunc_rev for introducing arginine at the insulin NB chain boundary.

```
3702_cjunc_rev
                                            (SEQ ID NO: 21)
5'-TCC ACGATGCCTCTGCGCTTCTG CAGGGACCC-3'
```

The codon for the arginine to be introduced is in bold print in both primers. A PCR is carried out in accordance with the European Patent Application EP-A 1 222 207 with each of the primer pairs Tir/3702_cjunc_rev and 3702_arg_cjuncf/pint3580_glya21rev and with DNA of the plasmid pINT3702 as template. Aliquots of the products of the two reactions are combined and employed together with the primer pair Tir/pint3580_glya21rev in a third PCR. The product of this reaction is purified after fractionation of the reaction mixture by gel electrophoresis and is digested with the restriction enzymes Sal1/Nco1 in accordance with the manufacturer's instructions in one and the same reaction, the reaction mixture is fractionated by gel electrophoresis, and the DNA fragment encoding the proinsulin sequence is isolated. The fragment is then inserted by a DNA ligase reaction into the Nco1/Sal1-opened pINT91d vector DNA.

The ligation mixture is used to transform competent *E. coli* bacterial cells. The transformation mixture is plated out on selection plates which contain 25 mg/l ampicillin. Plasmid DNA is isolated from colonies and characterized by DNA sequence analysis. Correct plasmids are called pINT3702.

The preproinsulin encoded by the plasmid is precursor for the compound Arg (A-1), Arg (A0), His (A8), Gly (A21), Arg (B30)-NH$_2$-human insulin. The compound is obtained by initially preparing the intermediate Arg (A-1), Arg (A0), His (A8), Gly (A21) of the Thr (B30)-human insulin by reaction with lysyl endopeptidase C, and the intermediate is subsequently converted by amidation with argininamide into the desired compound.

The preproinsulin encoded by the plasmid is precursor for the compound Arg (A-1), Arg (A0), His (A8), Gly (A21), Lys (B30)-NH$_2$-human insulin, which results after amidation with lysinamide.

It is clear to the skilled worker that aspartic acid or glutamic acid can be introduced into the appropriate positions of the A or B chain in accordance with Examples 3-8. These proinsulins are precursor for the compounds

| YKL202-10a | Arg (A-1), Arg (A0), Glu (A5), His (A8), Gly (A21), Arg (B30)-NH$_2$-human insulin |
|---|---|
| YKL202-10b | Arg (A-1), Arg (A0), Glu (A5), His (A8), Gly (A21), Lys (B30)-NH$_2$-human insulin |
| YKL202-11a | Arg (A-1), Arg (A0), Glu (A15), His (A8), Gly (A21), Arg (B30)-NH$_2$-human insulin |
| YKL202-11b | Arg (A-1), Arg (A0), Glu (A15), His (A8), Gly (A21), Lys (B30)-NH$_2$-human insulin |
| YKL202-12a | Arg (A-1), Arg (A0), Asp (A18), His (A8), Gly (A21), Arg (B30)-NH$_2$-human insulin |
| YKL202-12b | Arg (A-1), Arg (A0), Asp (A18), His (A8), Gly (A21), Arg (B30)-NH$_2$-human insulin |
| YKL202-13a | Arg (A-1), Arg (A0), His (A8), Gly (A21), Glu (B0), Arg (B30)-NH$_2$-human insulin |
| YKL202-13b | Arg (A-1), Arg (A0), His (A8), Gly (A21), Glu (B0), Lys (B30)-NH$_2$-human insulin |
| YKL202-14a | Arg (A-1), Arg (A0), His (A8), Gly (A21), Asp (B3), Arg (B30)-NH$_2$-human insulin |
| YKL202-14b | Arg (A-1), Arg (A0), His (A8), Gly (A21), Asp (B3), Lys (B30)-NH$_2$-human insulin |
| YKL202-15a | Arg (A-1), Arg (A0), His (A8), Gly (A21), Glu (B4), Arg (B30)-NH$_2$-human insulin |
| YKL202-15b | Arg (A-1), Arg (A0), His (A8), Gly (A21), Glu (B4), Lys (B30)-NH$_2$-human insulin |

Example 13

Preparation of the Vector Derivative pINT3704 which Codes for His (A8), Gly (A21), Lys (B0)-Preproinsulin This example describes the preparation of the vector derivative pINT3704 which codes for His (A8), Gly (A21), Lys (B0)-preproinsulin, and a modified C peptide which carries the tripeptide Lys-Arg-Arg at the C/A chain boundary and in which the amino acid glycine which occurs in position A21 in human insulin is deleted. Following the synthesis scheme described in Example 12 and replacing the primers 3702_arg_cjuncf and 3702_arg_cjuncfrev by the primers 3703_Δ Ga1f and 3703_Δ Ga1rev and using DNA of the plasmid pINT3703 as template results in the plasmid pINT3704 wherein the amino acid glycine in position 1 of the A chain is deleted in the encoded preproinsulin, and the remaining course of the sequence corresponds to that of the sequence encoded by pINT3703.

```
3703_Δ Ga1f
                                    (SEQ ID NO: 22)
5'-TGC AGAAGCGCAGAATCGTG GAGCAGTGCTGC-3'

3703_Δ Ga1rev
                                    (SEQ ID NO: 23)
5'-TGCTCC ACGATTCTGCGCTTCTG CAGGGACCC-3'
```

The preproinsulin encoded by the plasmid is precursor for the compound Arg (A0), Arg (A1), His (A8), Gly (A21), Arg (B30)-NH$_2$-human insulin. The compound is obtained by initially preparing the intermediate Arg (A0), Arg (A1), His (A8), Gly (A21), des Thr (B30)-human insulin by reaction with lysyl endopeptidase C, and the intermediate is then converted by amidation with argininamide into the desired compound.

The preproinsulin encoded by the plasmid is precursor for the compound Arg (A0), Arg (A1), His (A8), Gly (A21), Lys (B30)-NH$_2$-human insulin which results after amidation with lysinamide.

It is clear to the skilled worker that negatively charged amino acids can be introduced into the preproinsulin sequence in accordance with Example 12. It is also possible in analogy to Example 13 to prepare from the plasmid pINT3702 a plasmid that codes for a proinsulin sequence which permits the preparation of insulin derivatives which carry an arginine as N-terminal amino acid in position 1 of the A chain.

Example 14

Expression of the Proinsulin Derivatives

The expression is carried out in accordance with example 1 of European patent application EP-A 1 222 207.

Example 15

Folding of the Proinsulin Derivatives

The folding takes place in principle by the method described in EP-A 0 668 282

Example 16

Processing of the Proinsulins from Examples 2-8 with Trypsin

The folded preproinsulin is enzymatically processed to give the two-chain Arg (A0)-insulin precursor whose C-terminal B chain end is characterized by lysine or arginine. The enzymatic processing of the folded preproinsulin precursor takes place as described for example in example 4 of WO91/03550. It proves to be particularly advantageous in this case to employ the trypsin variant described in WO 2007/031187 A1.

Example 17

Processing of the Proinsulins from Examples 9-13 with Endoproteinase Lys-C

Endoprotease Lys-C from *Achromobacter lyticus* is commercially available (Merck/Calbiochem). The reaction is carried out with slight modification as described by Jekel, P. A. et al. [Anal. Biochem. 134, 347-354, (1983)]. A pH of 9.5 is set, and the reaction temperature is 30° C.

In the one-pot reaction, the presequence is eliminated and the C peptide starting with Thr (B30) is cleaved out, so that the C-terminal end of the B chain is formed by lysine which is present as reactive site for the enzyme-catalyzed coupling reaction.

Example 18

Preparation of the Arg-NH$_2$ or Lys-NH$_2$ Insulin Compound from the Two-Chain Precursor by Coupling with Arginin- or Lysinamide Irrespective of the positioning of the additional acidic amino acids, a standard reaction is carried out as follows: 100 mg of Arg (A0), Gly (A21), Arg (B31)-insulin analogue are dissolved in 0.95 ml of argininamide solution (446 g/L), and 0.13 mL of M Na acetate buffer (pH 5.8) and 2 ml of DMF are added. The reaction mixture is cooled to 12° C. and started by adding 0.094 ml of trypsin (0.075 mg, Roche Diagnostics). The reaction is stopped after 8 h by adding TFA to pH 2.5 and analyzed by HPLC. There is formation of >60% Arg (A0), Gly (A21), Arg (B31), Arg (B32)-NH$_2$-insulin analogue. Addition of trypsin inhibitor solution is followed by purification of the amidated analogue in analogy to U.S. Pat. No. 5,656,722.

Preparation of the corresponding lysinamide compound takes place analogously. However, an aqueous lysinamide stock solution containing 366 g/L lysinamide in solution forms the starting material.

Example 19

Semisynthetic Preparation of Lys (A-1), Arg (A0), His (A8), Gly (A21), Arg (B30)-Insulin Amide The compound YKL202-8 described in Example 11, which corresponds to an insulin derivative of the structure Arg (A0), His (A8), Gly (A21), Arg (B30)-insulin amide serves as starting material for preparing the compound YKL202-11, Lys (A-1), Arg (A0), His (A8), Gly (A21), Arg (B30)-insulin amide. 200 mg of the compound are dissolved in 40 ml of a 100 mM Na$_2$HPO$_4$/CH$_3$CN (50:50) mixture and a pH of 7.7-8.2 is set. As further material, a Boc-Lys (Boc)-NHS ester is prepared by mixing 0.3 mM Boc-Lys(Boc)-OH, 0.4 mM N-hydroxysuccinimide (NHS) and 0.4 mM dicyclohexylcarbodiimide (DCC) in dichloromethane for 40 minutes. The reaction mixture is concentrated to dryness in a rotary vacuum evaporator. The mixture is then taken up in 5 ml of methanol and added to the dissolved initial insulin. The reaction is stirred at room temperature for at least 60, but at most 120, minutes. The reaction is stopped by adding 200 µl of TFA. The mass of the reaction products is characterized by LC-MS mass spectroscopy in order to demonstrate that monoacylated product consisting of three components is present. The components are separated by HPLC. During this, diacylated and triacylated byproducts are also removed. The fractions from the HPLC separation are analyzed by mass spectroscopy. The 3 fractions each containing monoacylated product are subjected to an amino acid sequence analysis, interpretation of which allows identification of the HPLC fraction which contains the desired compound, from which the Boc protective groups are subsequently removed by hydrolysis. After renewed HPLC purification, the desired product is tested for its biological properties.

Example 20

Preparation of the Plasmid pINT358_ha8 which Codes for His (A8), Gly (A21) Proinsulin Following the preparation scheme from Example 2 and using DNA of the plasmid pINT358d as template for PCR1 and PCR2 results in the plasmid pINT358_ha8 which codes for His (A8), Gly (A21) proinsulin. The proinsulin encoded by the plasmid serves as precursor for the compound of the form His (A8), Gly (A21), Arg (B31), Arg (B32)-NH$_2$-human insulin. Processing of the preproinsulin to give His (A8), Gly (A21), Arg (B31) as intermediate before amidation takes place as described in WO91/03550 in this case. Conventional trypsin is employed in this case.

Example 21

Formulation of the Amidated Insulin Derivatives

In order to test the insulin derivatives of the invention for their biopharmacological and physicochemical properties, a solution of the compounds was prepared as follows: the insulin derivative of the invention was dissolved with a target concentration of 240±5 µM in 1 mM hydrochloric acid with 80 µg/mL zinc (as zinc chloride). For this purpose, initially an amount of the freeze-dried material which is about 30% higher than required on the basis of the molecular weight and the desired concentration was weighed out. The concentration present was then determined by analytical HPLC and the solution was subsequently made up to the volume necessary to achieve the target concentration with 5 mM hydrochloric acid with 80 µg/mL zinc. If necessary, the pH was readjusted to 3.5±0.1. After the final analysis by HPLC to verify the target concentration of 240±5 µM, the finished solution was transferred by means of a syringe with a 0.2 µm filter attachment into a sterile vial which was closed with a septum and a crimped cap. No optimization of the formulations, e.g. in relation to addition of isotonic agents, preservatives or buffer substances, was carried out for the short-term single testing of the insulin derivatives of the invention.

Example 22

Preparation of His (A8), Gly (A21), Arg(B31) Human Insulin by Yeast Expression

EP-A 1 364 032 describes the expression and secretion of a fusion protein of hirudin and miniproinsulin by yeast. Yeast host organisms which are mentioned as particularly advantageous in this connection are *S. cerevisiae*, *K. lactis*, *H. polymorpha* and *P. pastoris*. Example 4 of said patent application describes the construction of a plasmid which permits preparation of the fusion protein in *P. pastoris* and whose DNA serves as template for preparing a miniproinsulin whose amino acid sequence in positions A8, A15, A18 and A21 in the A chain is characterized by the amino acids histidine (A8), glutamic acid (A15), aspartic acid (A18) and glycine (A21). The primer *pichia_H_if1* is used. The following primers are newly synthesized and purified after synthesis:

```
pichia_G21_rev
                                    (SEQ ID NO: 24)
5'-TTTTTTGGCG CCGAATTCAC TATTAGCCAC AGTAGTTTTC

CAGCTGGTA-3'
```

The codon emphasized by emboldening marks the A21 positions.

```
pichia_H8_f with the sequence
                                      (SEQ ID NO: 25)
5'-GAACAATGTTGTCATAGTATCTGTTCTTTGTACCAGCTGGAAAAC

TACTG-3'
```

The codon emphasized by emboldening marks the A8 positions.

```
    pichia-a1-12rev
                                      (SEQ ID NO: 25)
    5'-GAACAGATACTATGACAACATTGTTCAACGATACC-3'
```

The codon emphasized by emboldening marks the A8 positions.

Equimolar amounts (1 μg) of primer pichia_G21_rev and primer pichia_H8f, which partially overlap, are denatured at 95° C. in the presence of a thermophilic polymerase and polymerase buffer which contains the 4 deoxynucleotides dATP, dCTP, dGTP and dTTP 5', and then incubated at 56° C. for 10-15 minutes. The reaction volume of this reaction 1 is 25 μl. In a standard polymerase chain reaction (reaction 2), the primers pichia_H_if1 and pichia-a1-12rev are reacted in parallel with the described template DNA. In a further polymerase chain reaction, the reaction products of reactions 1 and 2 are reacted as template with the primers pichia_H_if1/pichia_G21rev. The reaction product of this reaction is purified by gel electrophoresis. After reaction with the restriction enzymes XhoI and SacII, the DNA fragment which covers the fusion product is inserted into the described vector pPICZαA in analogy to Example 4. The result is the plasmid pPIC_ins202. Fusion protein encoded by the plasmid is expressed using the commercially available expression kit described. Preparation of the His (A8), Gly (A21), Arg (B31)-human insulin precursor is followed by the coupling of arginine amide in accordance with the description on arginine (B31). The result is the compound His (A8), Gly (A21), Arg (B31), Arg (B32)-NH$_2$-insulin (YKL203) which itself represents a novel slow insulin corresponding to Example 20 and is tested in the rat experiment. Coupling with lysine amide leads analogously to the compound YKL203b which is characterized as His (A8), Gly (A21), Arg (B31), Lys (B32)-NH$_2$-insulin.

The compound can, however, also serve as intermediate for preparing the compound Arg (A0), His (A8), Gly (A21), Arg (B31) Arg(B32)-NH$_2$-insulin whose preparation is based on Kohn et al. [Peptides 28 (2007) 935-948]. For this purpose, 200 mg of the compound His (A8), Gly (A21), Arg (B31), Arg (B32)-NH$_2$-human insulin are dissolved in 40 ml of a mixture of 100 mM Na$_2$HPO$_4$/CH$_3$CN (50:50) and a pH of 7.7-8.2 is set.

As further material, a Boc-Arg-NHS ester is prepared by mixing 0.3 mM Boc-Arg-OH, 0.4 mM N-hydroxysuccinimide (NHS) and 0.4 mM dicyclohexylcarbodiimide (DCC) in dichloromethane for 40 minutes. The reaction mixture is concentrated to dryness in a rotary vacuum evaporator. The mixture is then taken up in 5 ml of methanol and added to the dissolved initial insulin. The reaction is stirred at room temperature for at least 60, but at most 120, minutes. The reaction is stopped by adding 200 μl of TFA. The mass of the reaction products is characterized by LC-MS mass spectroscopy in order to demonstrate that monoacylated product consisting of three components is present. The components are separated by HPLC. During this, diacylated and triacylated byproducts are also removed. The fractions from the HPLC separation are analyzed by mass spectroscopy. The three fractions each containing monoacylated product are subjected to an amino acid sequence analysis, interpretation of which allows identification of the HPLC fraction which contains the desired compound, from which the Boc protective groups are subsequently removed by gentle hydrolysis. After renewed HPLC purification, the desired product is tested for its biological properties.

Example 23

Evaluation of the Blood Glucose-Lowering Effect of Novel Insulin Analogues in Rats The blood glucose-lowering effect of selected novel insulin analogues is tested in healthy male normal glycemic Wistar rats. Male rats receive subcutaneous injection of a dose of 9 nmol/kg of an insulin analogue. Blood samples are taken from the animals immediately before the injection of the insulin analogue and at regular intervals up to eight hours after the injection, and the blood glucose content therein is determined. The experiment shows clearly (cf. FIG. 1) that the insulin analogue of the invention leads to a distinctly delayed onset of action and a longer, uniform duration of action.

Example 24

Evaluation of the Blood Glucose-Lowering Effect of Novel Insulin Analogues in Dogs The blood glucose-lowering effect of selected novel insulin analogues is tested in healthy male normoglycemic beagle dogs. Male animals receive subcutaneous injection of a dose of 6 nmol/kg of an insulin analogue. Blood samples are taken from the animals immediately before the injection of the insulin analogue and at regular intervals up to 48 hours after the injection, and the blood glucose content therein is determined. The experiment shows clearly that the insulin analogue of the invention leads to a distinctly delayed shallow onset of action and a longer, uniform duration of action.

What is claimed is:

1. An insulin analogue of the formula I:

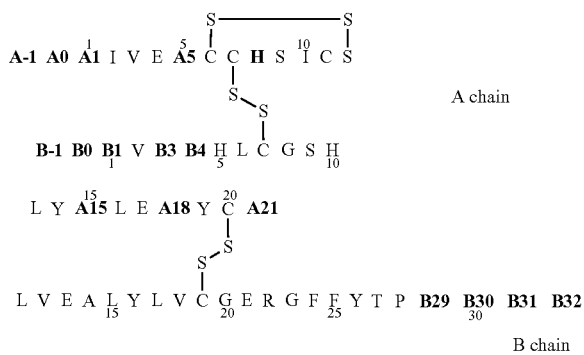

wherein
A-1 corresponds to Lys, Arg or an amino group;
A0 corresponds to Lys, Arg or a chemical bond;
A1 corresponds to Arg or Gly;
A5 corresponds to Asp, Glu or Gln;
A15 corresponds to Asp, Glu or Gln;
A18 corresponds to Asp, Glu or Asn;
A21 corresponds to Ala, Ser, Thr or Gly;
B-1 corresponds to Asp, Glu or an amino group;
B0 corresponds to Asp, Glu or a chemical bond;
B1 corresponds to Asp, Glu, Phe or a chemical bond;
B3 corresponds to Asp, Glu or Asn;
B4 corresponds to Asp, Glu or Gln;
B29 corresponds to Arg, Lys or an amino acid selected from the group comprising the amino acids Phe, Ala, Thr, Ser, Val, Leu, Glu or Asp, or a chemical bond;
B30 corresponds to Thr or a chemical bond;
B31 corresponds to Arg, Lys or a chemical bond;
B32 corresponds to Arg-amide or Lys-amide; and
wherein no more than one amino acid residue of the group comprising A5, A15, A18, B-1, B0, B1, B2, B3 and B4 correspond simultaneously and independently of one another to Asp or Glu.

2. The insulin analogue as claimed in claim 1, wherein A-1 corresponds to Arg.

3. The insulin analogue as claimed in claim 1, wherein A0 corresponds to Arg.

4. The insulin analogue as claimed in claim 1, wherein A5 corresponds to Glu.

5. The insulin analogue as claimed in claim 1, wherein A15 corresponds to Glu.

6. The insulin analogue as claimed in claim 1, wherein A18 corresponds to Asp.

7. The insulin analogue as claimed in claim 1, wherein A8 corresponds to His.

8. The insulin analogue as claimed in claim 1, wherein A21 corresponds to Gly.

9. The insulin analogue as claimed in claim 1, wherein B0 corresponds to Glu.

10. The insulin analogue as claimed in claim 1, wherein B3 corresponds to Asp.

11. The insulin analogue as claimed in claim 1, wherein B4 corresponds to Glu.

12. The insulin analogue as claimed in claim 1, wherein B30 corresponds to Arg.

13. The insulin analogue as claimed in claim 1, wherein B30 corresponds to Lys.

14. The insulin analogue as claimed in claim 1, which is Arg (A0), His (A8), Gly (A21), Arg (B31), Arg (B32) $NH_2$ human insulin.

15. A pharmaceutical composition comprising an insulin analogue as claimed in claim 1 or a physiologically acceptable salt thereof.

16. A formulation of the insulin analogue as claimed in claim 1, wherein the formulation is in aqueous form comprising the dissolved insulin analogue.

17. The formulation as claimed in claim 16, which additionally comprises a glucagon-like peptide-1 (GLP 1) or an analogue thereof, or exendin-3 or -4 or an analogue thereof.

18. The formulation as claimed in claim 17, which additionally comprises exendin-4.

19. The formulation as claimed in claim 18, wherein an analogue of exendin-4 is selected from a group comprising
H-desPro$^{36}$-exendin-4-Lys$_6$-NH$_2$,
H-des(Pro$^{36,37}$)-exendin-4-Lys$_4$-NH$_2$ and
H-des(Pro$^{36,37}$)-exendin-4-Lys$_5$-NH$_2$,
or a pharmacologically tolerable salt thereof.

20. The formulation as claimed in claim 18, wherein an analogue of exendin-4 is selected from a group comprising
desPro$^{36}$ [Asp$^{28}$]exendin-4 (1-39),
desPro$^{36}$ [IsoAsp$^{28}$]exendin-4 (1-39),
desPro$^{36}$ [Met(O)$^{14}$, Asp$^{28}$]exendin-4 (1-39),
desPro$^{36}$ [Met(O)$^{14}$, IsoAsp$^{28}$]exendin-4 (1-39),
desPro$^{36}$ [Trp(O$_2$)$^{25}$, Asp$^{28}$]exendin-2 (1-39),
desPro$^{36}$ [Trp(O$_2$)$^{25}$, IsoAsp$^{28}$]exendin-2 (1-39),
desPro$^{36}$ [Met(O)$^{14}$Trp(O$_2$)$^{25}$, Asp$^{28}$]exendin-4 (1-39) and
desPro$^{36}$ [Met(O)$^{14}$Trp(O$_2$)$^{25}$, IsoAsp$^{28}$]exendin-4 (1-39),
or a pharmacologically tolerable salt thereof.

21. The formulation as claimed in claim 18, wherein the peptide -Lys$_6$-NH$_2$ is attached to the C termini of the analogues of exendin-4.

22. The formulation as claimed in claim 18, wherein an analogue of exendin-4 is selected from a group consisting of:
H-(Lys)$_6$-des Pro$^{36}$ [Asp$^{28}$]exendin-4(1-39)-Lys$_6$-NH$_2$
des Asp$^{28}$Pro$^{36}$, Pro$^{37}$, Pro$_{38}$ exendin-4(1-39)-NH$_2$,
H-(Lys)$_6$-des Pro$^{36}$, Pro$^{37}$, Pro$^{38}$ [Asp$^{28}$]exendin-4(1-39)-NH$_2$,
H-Asn-(Glu)$_5$ des Pro$^{36}$, Pro$^{37}$, Pro$^{38}$ [Asp$^{28}$]exendin-4(1-39)-NH$_2$,
des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$, Pro$^{37}$, Pro$^{38}$ [Asp$^{28}$]exendin-4(1-39)-(Lys)$_6$-NH$_2$,
H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$ [Trp(O$_2$)$^{25}$, Asp$^{28}$]exendin-4(1-39)-Lys$_6$-NH$_2$, H-des Asp$^{28}$ Pro$^{36}$, Pro$^{37}$, Pro$^{38}$ [Trp(O$_2$)$^{25}$]exendin-4(1-39)-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Trp(O$_2$)$^{25}$, Asp$^{28}$] exendin-4(1-39)-NH$_2$,
des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$] exendin-4(1-39)-(Lys)$_6$-NH$_2$,
H-(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$,
des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$]exendin-4(1-39)-Lys$_6$-NH$_2$,
H-Asn-(Glu)$_5$ des Pro$^{36}$, Pro$^{37}$, Pro$^{38}$ [Met(O)$^{14}$, Asp$^{28}$] exendin-4(1-39)-(Lys)$_6$-NH$_2$,
H-(Lys)$_6$-des Pro$^{36}$ [Met(O)$^{14}$, Trp(O$_2$)$^{25}$, Asp$^{28}$]exendin-4(1-39)-Lys$_6$-NH$_2$,
des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Met(0)$^{14}$, Asp$^{28}$] exendin-4(1-39)-NH$_2$,
des Pro$^{36}$, Pro$^{37}$, Pro$^{38}$ [Met(0)$^{14}$, Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$,
or a pharmacologically tolerable salt thereof.

23. The formulation as claimed in claim 18, which additionally comprises Arg$^{34}$, Lys$^{26}$ (N$^\epsilon$(γ-glutamyl(N$^\alpha$-hexadecanoyl))) GLP-1 (7-37) [liraglutide].

24. A formulation of the insulin analogue as claimed in claim 1, wherein the formulation is in the form of a powder.

25. The formulation as claimed in claim 24, wherein the insulin analogue as claimed in claim 1 is present in crystalline or amorphous form.

26. A formulation of the insulin analogue as claimed in claim 1, wherein the formulation is in the form of a suspension.

27. A formulation of the insulin analogue as claimed in claim 1, wherein the formulation additionally comprises a chemical chaperone.

* * * * *

SEQUENCE LISTING

```
<160> NUMBER OF SEQ ID NOS: 26

<210> SEQ ID NO 1
<211> LENGTH: 23
<212> TYPE: PRT
<213> ORGANISM: Artificial Sequence
<220> FEATURE:
<223> OTHER INFORMATION: A-Chain of insulin analogue of formula I
```

```
<220> FEATURE:
<221> NAME/KEY: misc_feature
<222> LOCATION: (1)..(1)
<223> OTHER INFORMATION: Xaa can be Lys, Arg or absent
<220> FEATURE:
<221> NAME/KEY: misc_feature
<222> LOCATION: (2)..(2)
<223> OTHER INFORMATION: Xaa can be Lys, Arg or absent
<220> FEATURE:
<221> NAME/KEY: misc_feature
<222> LOCATION: (3)..(3)
<223> OTHER INFORMATION: Xaa can be Arg or Gly
<220> FEATURE:
<221> NAME/KEY: misc_feature
<222> LOCATION: (7)..(7)
<223> OTHER INFORMATION: Xaa can be Asp, Glu or Gln
<220> FEATURE:
<221> NAME/KEY: misc_feature
<222> LOCATION: (17)..(17)
<223> OTHER INFORMATION: Xaa can be Asp, Glu or Gln
<220> FEATURE:
<221> NAME/KEY: misc_feature
<222> LOCATION: (20)..(20)
<223> OTHER INFORMATION: Xaa can be Asp, Glu or Asn
<220> FEATURE:
<221> NAME/KEY: misc_feature
<222> LOCATION: (23)..(23)
<223> OTHER INFORMATION: Xaa can be Ala, Ser, Thr or Gly

<400> SEQUENCE: 1

Xaa Xaa Xaa Ile Val Glu Xaa Cys Cys His Ser Ile Cys Ser Leu Tyr
1               5                   10                  15

Xaa Leu Glu Xaa Tyr Cys Xaa
            20

<210> SEQ ID NO 2
<211> LENGTH: 34
<212> TYPE: PRT
<213> ORGANISM: Artificial Sequence
<220> FEATURE:
<223> OTHER INFORMATION: B-Chain of insulin analogue of formula I
<220> FEATURE:
<221> NAME/KEY: misc_feature
<222> LOCATION: (1)..(1)
<223> OTHER INFORMATION: Xaa can be Asp, Glu or absent
<220> FEATURE:
<221> NAME/KEY: misc_feature
<222> LOCATION: (2)..(2)
<223> OTHER INFORMATION: Xaa can be Asp, Glu or absent
<220> FEATURE:
<221> NAME/KEY: misc_feature
<222> LOCATION: (3)..(3)
<223> OTHER INFORMATION: Xaa can be Asp, Glu, Phe or absent
<220> FEATURE:
<221> NAME/KEY: misc_feature
<222> LOCATION: (5)..(5)
<223> OTHER INFORMATION: Xaa can be Asp, Glu or Asn
<220> FEATURE:
<221> NAME/KEY: misc_feature
<222> LOCATION: (6)..(6)
<223> OTHER INFORMATION: Xaa can be Asp, Glu or Gln
<220> FEATURE:
<221> NAME/KEY: misc_feature
<222> LOCATION: (31)..(31)
<223> OTHER INFORMATION: Xaa can be Arg, Lys or an amino acid selected
      from the group comprising the amino acids Phe, Ala, Thr, Ser,
      Val, Leu, Glu or Asp, or absent
<220> FEATURE:
<221> NAME/KEY: misc_feature
<222> LOCATION: (32)..(32)
<223> OTHER INFORMATION: Xaa can be Thr or absent
<220> FEATURE:
<221> NAME/KEY: misc_feature
<222> LOCATION: (33)..(33)
<223> OTHER INFORMATION: Xaa can be Arg, Lys or absent
<220> FEATURE:
<221> NAME/KEY: misc_feature
```

```
<222> LOCATION: (34)..(34)
<223> OTHER INFORMATION: Xaa can be Arg-amide or Lys-amide

<400> SEQUENCE: 2

Xaa Xaa Xaa Val Xaa Xaa His Leu Cys Gly Ser His Leu Val Glu Ala
1               5                   10                  15

Leu Tyr Leu Val Cys Gly Glu Arg Gly Phe Phe Tyr Thr Pro Xaa Xaa
            20                  25                  30

Xaa Xaa

<210> SEQ ID NO 3
<211> LENGTH: 38
<212> TYPE: DNA
<213> ORGANISM: Artificial Sequence
<220> FEATURE:
<223> OTHER INFORMATION: Synthetic oligonucleotide primer designated as
      pint3580_glya21rev

<400> SEQUENCE: 3
caaaggtcga ctattagccg cagtagttct ccagctgg                              38

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide primer designated as
      arg_cjuncf

<400> SEQUENCE: 4
gtccctgcag cgtcgcggca tcgtggagca g                                     31

<210> SEQ ID NO 5
<211> LENGTH: 36
<212> TYPE: DNA
<213> ORGANISM: Artificial Sequence
<220> FEATURE:
<223> OTHER INFORMATION: Synthetic oligonucleotide primer designated as
      arg_cjunc_rev

<400> SEQUENCE: 5
ccacgatgcc gcgacgctgc agggacccct ccagcg                                36

<210> SEQ ID NO 6
<211> LENGTH: 32
<212> TYPE: DNA
<213> ORGANISM: Artificial Sequence
<220> FEATURE:
<223> OTHER INFORMATION: Synthetic oligonucleotide primer designated as
      pint3580_Ha8f

<400> SEQUENCE: 6
agcagtgctg ccacagcatc tgctccctct ac                                    32

<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide primer designated as
      pint3580_Ha8rev

<400> SEQUENCE: 7
gagcagatgc tgtggcagca ctgctccacg atg                                   33

<210> SEQ ID NO 8
```

```
<211> LENGTH: 31
<212> TYPE: DNA
<213> ORGANISM: Artificial Sequence
<220> FEATURE:
<223> OTHER INFORMATION: Synthetic oligonucleotide primer designated as
      pint3581_Ea5f

<400> SEQUENCE: 8
gcatcgtgga ggagtgctgc cacagcatct g                                          31

<210> SEQ ID NO 9
<211> LENGTH: 32
<212> TYPE: DNA
<213> ORGANISM: Artificial Sequence
<220> FEATURE:
<223> OTHER INFORMATION: Synthetic oligonucleotide primer designated as
      pint3581_Ea5rev

<400> SEQUENCE: 9
ctgtggcagc actcctccac gatgccgcga cg                                         32

<210> SEQ ID NO 10
<211> LENGTH: 47
<212> TYPE: DNA
<213> ORGANISM: Artificial Sequence
<220> FEATURE:
<223> OTHER INFORMATION: Synthetic oligonucleotide primer designated as
      pint3580_Da18rev

<400> SEQUENCE: 10
caaaggtcga ctattagccg cagtagtcct ccagctggta gagggag                         47

<210> SEQ ID NO 11
<211> LENGTH: 56
<212> TYPE: DNA
<213> ORGANISM: Artificial Sequence
<220> FEATURE:
<223> OTHER INFORMATION: Synthetic oligonucleotide primer designated as
      pint3580_Ea15rev

<400> SEQUENCE: 11
caaaggtcga ctattagccg cagtagttct ccagctcgta gagggagcag atgctg               56

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide primer designated as
      pint3581_Db3f

<400> SEQUENCE: 12
gcacgatttg tggaccagca cctgtgcggc                                            30

<210> SEQ ID NO 13
<211> LENGTH: 34
<212> TYPE: DNA
<213> ORGANISM: Artificial Sequence
<220> FEATURE:
<223> OTHER INFORMATION: Synthetic oligonucleotide primer designated as
      pint3581_Db3rev

<400> SEQUENCE: 13
cacaggtgct ggtccacaaa tcgtgccgaa tttc                                       34

<210> SEQ ID NO 14
<211> LENGTH: 30
<212> TYPE: DNA
```

<213> ORGANISM: Artificial Sequence
<220> FEATURE:
<223> OTHER INFORMATION: Synthetic oligonucleotide primer designated as
      pint3581_Eb4f

<400> SEQUENCE: 14
acgatttgtg aacgagcacc tgtgcggctc                                    30

<210> SEQ ID NO 15
<211> LENGTH: 36
<212> TYPE: DNA
<213> ORGANISM: Artificial Sequence
<220> FEATURE:
<223> OTHER INFORMATION: Synthetic oligonucleotide primer designated as
      pint3581_Eb4rev

<400> SEQUENCE: 15
cgcacaggtg ctcgttcaca aatcgtgccg aatttc                             36

<210> SEQ ID NO 16
<211> LENGTH: 43
<212> TYPE: DNA
<213> ORGANISM: Artificial Sequence
<220> FEATURE:
<223> OTHER INFORMATION: Synthetic oligonucleotide primer designated as
      pint3581_Eb0f1

<400> SEQUENCE: 16
caacaggaaa ttcggcacga gagtttgtga accagcacct gtg                     43

<210> SEQ ID NO 17
<211> LENGTH: 44
<212> TYPE: DNA
<213> ORGANISM: Artificial Sequence
<220> FEATURE:
<223> OTHER INFORMATION: Synthetic oligonucleotide primer designated as
      pint3581_Eb01f2

<400> SEQUENCE: 17
tatcgaccat ggcaacaaca tcaacaggaa attcggcacg agag                    44

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide primer designated as
      pint3581_Eb0f1

<400> SEQUENCE: 18
caacaggaaa ttcggcaaag tttgtgaacc agcacctgtg                         40

<210> SEQ ID NO 19
<211> LENGTH: 41
<212> TYPE: DNA
<213> ORGANISM: Artificial Sequence
<220> FEATURE:
<223> OTHER INFORMATION: Synthetic oligonucleotide primer designated as
      pint3581_Eb01f2

<400> SEQUENCE: 19
tatcgaccat ggcaacaaca tcaacaggaa attcggcaga g                       41

<210> SEQ ID NO 20
<211> LENGTH: 32
<212> TYPE: DNA
<213> ORGANISM: Artificial Sequence
<220> FEATURE:

-continued

<223> OTHER INFORMATION: Synthetic oligonucleotide primer designated as
     3702_arg_cjuncf

<400> SEQUENCE: 20
tgcagaagcg cagaggcatc gtggagcagt gc                                    32

<210> SEQ ID NO 21
<211> LENGTH: 32
<212> TYPE: DNA
<213> ORGANISM: Artificial Sequence
<220> FEATURE:
<223> OTHER INFORMATION: Synthetic oligonucleotide primer designated as
     3702_cjunc_rev

<400> SEQUENCE: 21
tccacgatgc ctctgcgctt ctgcagggac cc                                    32

<210> SEQ ID NO 22
<211> LENGTH: 32
<212> TYPE: DNA
<213> ORGANISM: Artificial Sequence
<220> FEATURE:
<223> OTHER INFORMATION: Synthetic oligonucleotide primer designated as
     3703_delta Ga1f

<400> SEQUENCE: 22
tgcagaagcg cagaatcgtg gagcagtgct gc                                    32

<210> SEQ ID NO 23
<211> LENGTH: 32
<212> TYPE: DNA
<213> ORGANISM: Artificial Sequence
<220> FEATURE:
<223> OTHER INFORMATION: Synthetic oligonucleotide primer designated as
     3703_delta Ga1rev

<400> SEQUENCE: 23
tgctccacga ttctgcgctt ctgcagggac cc                                    32

<210> SEQ ID NO 24
<211> LENGTH: 49
<212> TYPE: DNA
<213> ORGANISM: Artificial Sequence
<220> FEATURE:
<223> OTHER INFORMATION: Synthetic oligonucleotide primer designated as
     pichia_G21_rev

<400> SEQUENCE: 24 tttttttggcg ccgaattcac tattagccac agtagttttc cagctggta                 49

<210> SEQ ID NO 25
<211> LENGTH: 50
<212> TYPE: DNA
<213> ORGANISM: Artificial Sequence
<220> FEATURE:
<223> OTHER INFORMATION: Synthetic oligonucleotide primer designated as
     pichia_H8_f

<400> SEQUENCE: 25
gaacaatgtt gtcatagtat ctgttctttg taccagctgg aaaactactg                 50

<210> SEQ ID NO 26
<211> LENGTH: 35
<212> TYPE: DNA
<213> ORGANISM: Artificial Sequence
<220> FEATURE:
<223> OTHER INFORMATION: Synthetic oligonucleotide primer designated as
     pichia-a1-12rev

```
<400> SEQUENCE: 26
gaacagatac tatgacaaca ttgttcaacg atacc                    35
```